United States Patent [19]
Donahoe et al.

[11] Patent Number: 5,310,880
[45] Date of Patent: May 10, 1994

[54] PURIFICATION OF MULLERIAN INHIBITING SUBSTANCE

[75] Inventors: Patricia K. Donahoe, Weston; Richard C. Ragin, Brayton; David T. MacLaughkin, Saugus, all of Mass.

[73] Assignee: The General Hospital Corporation, Boston, Mass.

[21] Appl. No.: 683,957

[22] Filed: Apr. 12, 1991

[51] Int. Cl.$^5$ .................... C07K 3/20; C07K 15/06; C07K 15/14
[52] U.S. Cl. .................... 530/395; 530/397; 530/413
[58] Field of Search ............ 530/395, 397, 399, 413

[56] References Cited

U.S. PATENT DOCUMENTS

| | | | |
|---|---|---|---|
| 4,404,188 | 9/1983 | Donahoe et al. | 424/105 |
| 4,487,833 | 12/1984 | Donahoe et al. | 435/70.21 |
| 4,510,131 | 4/1985 | Donahoe et al. | 530/399 |
| 4,753,794 | 6/1988 | Donahoe | 530/397 |
| 4,792,601 | 12/1988 | Donahoe et al. | 530/387 |
| 5,010,055 | 4/1991 | Donahoe et al. | 514/8 |
| 5,011,687 | 4/1991 | Donahoe et al. | 514/8 |
| 5,047,336 | 9/1991 | Cate et al. | 435/69.4 |

OTHER PUBLICATIONS

Harris et al, *Protein Purification Methods* IRL Press. 1989, pp. 282, 286–289.
Cate et al, "Isolation of the Bovine and Human Genes for Mullerian Inhibiting Substance . . . ". *Cell*, Jun. 6, 1986. vol. 45, pp. 685–698.
Shima et al, "Production of Monoclonal Antibodies for Affinity Purification of Bovine Mullerian . . . ", *Hybridona*. 1984. vol. 3(3). pp. 201–214.
Donahoe et al., *Science*, 205:913-15 (1979).
Pepinsky et al., *J. Biol. Chem.*, 263(35):18961-4 (1988).
Fuller et al., *J. Clin. Endocrinol. Metab.*, 54(5):1051-5 (1982).
Fuller et al., *Gynecol. Oncol.*, 22:135-48 (1985).
Wallen et al., *Cancer Res.*, 49:2005-11 (1989).
Epstein et al., *In Vitro Cell. and Devel. Biol.*, 25(2):213-6 (1989).
Hudson, et al., *J. Clin. Endocrinol. Metab.*, 70(1):16-22 (1990).
Cate et al., "Mullerian-Inhibiting Substance" in *Handbook of Experimental Pharmacology*, 95/II:179-210 (1990).
Chin et al., *Cancer Res.*, 51 (8):2101-06 (Apr. 15, 1991).

*Primary Examiner*—Jeffrey E. Russel
*Attorney, Agent, or Firm*—Sterne, Kessler, Goldstein & Fox

[57] ABSTRACT

The present invention discloses a method of purifying Mullerian Inhibiting Substance. The method takes advantage of immunoaffinity chromatography to achieve MIS at up to 95 % purity. The method provides for a purified MIS product in which contaminating enzymes having MIS proteolytic activity or inhibitors of MIS antiproliferative activity are substantially removed by addition of an alkali metal halide solution or an alkaline earth metal halide solution prior to elution with an acid solution having a pH of between about 2.5 and 4.0.

9 Claims, 3 Drawing Sheets

← Pre-Pro Sequence →

Human  Met Arg Asp Leu Pro Leu Thr Ser Leu Ala Leu Val Leu Ser Ala Leu Leu Gly Ala Leu Leu Gly Thr Glu Ala Leu Arg
Bovine       Met Pro Gly Pro Ser Leu Ser Leu Ala Leu Leu Val Leu Ala Leu Ala Met Gly Ala Leu Leu Arg Gly Thr Pro Arg
Rat          Met Gln Gly Pro His Leu Ser Leu Leu Leu Leu Leu Ala Thr Met Gly Ala Val Leu Ala Val Leu Gln Ala Ala Asp Thr Val Human   Ala Glu ........ Glu Pro Ala Val Gly Thr Ser Gly Leu Ile Phe Arg Glu Asp Leu Asp Trp Pro ........
Bovine  Glu Glu Val Phe Ser Thr Ser Ala Leu Pro Arg Glu Gln Ala Thr Gly Ser Gly Ala Leu Ile Phe Gln Gln Ala Trp Asp Trp Pro Leu Ser
Rat     Glu Glu Leu Thr Asn Thr Arg Gly Leu ........                                                    Ile Phe Leu Glu Asp Human   ........ Pro Gly Ile Pro Gln Glu Pro Leu Cys Leu Val Ala Leu Gly Gly Asp Ser Ser Ser Pro Leu Arg Val Val
Bovine  Ser Leu Trp Leu Pro Gly Ser Pro Leu Asp Pro Leu Cys Leu Val Thr Leu His Gly Ser Gly Asn Gly Ser Arg Ala Pro Leu Arg Val Val
Rat     Gly Val Trp Pro Pro Pro Ser Leu Val Ala Gly Val Gln Gly Asp Thr Ser Lys Ala Ser Leu Thr Val Val Human   Gly Ala Leu Ser Ala Tyr Glu Gln Ala Phe Leu Gly Ala Val Gln Arg Ala Arg Trp Gly Pro Arg Asp Leu Ala Thr Phe Gly Val Cys Asn
Bovine  Gly Val Leu Ser Ser Tyr Glu Gln Ala Phe Leu Gly Ala Val Gln Arg Ala Arg Trp His Trp Gly Leu Ser Asp Leu Thr Thr Phe Ala Val Cys Pro
Rat     Gly Gly Leu His Ser Tyr Glu Gln Ala Phe Leu Gly Ala Val Gln Gln Ala Arg Trp Gly Pro Gln Asp Leu Ala Thr Phe Gly Val Cys ...

Human   Thr Gly Asp Arg Gln Ala Ala Leu Pro Ser Leu Arg Arg Leu Gly Ala Trp Leu Arg Asp Pro Gly Gly Gln Arg Leu Val Val Leu His Leu
Bovine  Ala Gly Asn Gly Gln Thr Gln Gly Pro Val Leu Pro His Leu Gln Arg Leu Gln Arg Leu Gly Pro Gly Gly Gly Arg Trp Leu Val Val Leu His Leu
Rat     Ser Thr Asp Ser Gln Thr Leu Pro Ala Leu Leu Gly Leu Ala Trp Leu Ala Trp Leu Gly Leu Thr Gly Glu Gln Leu Val Val Leu His Leu Human   Glu Glu Val Thr Trp Glu Pro Thr Pro Ser Leu Arg Phe Gln Glu Pro Pro Pro Gly Gly Ala Gly Pro Gln Leu Ala Leu Leu Val Leu
Bovine  Glu Glu Val Thr Trp Glu Pro Thr Pro Leu Leu Arg Phe Gln Glu Gln Leu Pro Pro Gly Gly Leu Ala Ser Pro Pro Gly Leu Ala Leu Leu Val Val
Rat     Ala Glu Val Ile Trp Glu Pro Gln Pro Gln Leu Leu Leu Lys Phe Gln Leu Gly Leu Pro Pro Pro Gly Gly Ala Ser Arg Trp Gln Ala Leu Leu Val Leu + = Cys   X = Leu Rep   ■ = CHO site   - = Tyr   | = Cleavage Site

FIG.1A

|  | | |
|---|---|---|
| Human | Tyr Pro Gly Pro Glu Val Thr Arg Ala Gly Leu Pro Gly Ala Gln Ser Leu Cys Pro Ser Arg Asp Thr Arg Tyr Leu Val | − |
| Bovine | Tyr Pro Gly Pro Leu Glu Val Thr Val Thr Gly Ala Gly Leu Pro Gly Thr Gln Ser Leu Cys Leu Thr Ala Asp Ser Asp Phe Leu Ala | |
| Rat | Tyr Pro Gly Pro Gln Val Thr Val Thr Gly Ala Gly Leu Gln Gly Thr Gln Ser Leu Cys Pro Thr Arg Asp Thr Arg Tyr Leu Val | |

|  | | |
|---|---|---|
| Human | Leu Ala Val Asp Arg Pro Ala Gly Ala Trp Arg Gly Ser Gly Leu Ala Leu Thr Leu Gln Pro Arg Gly Glu Asp Ser Arg Leu Ser Thr Ala | + |
| Bovine | Leu Val Val Asp His Pro Glu Gly Ala Trp Arg Arg Pro Gly Leu Ala Leu Thr Leu Leu Arg Arg Arg Gly Asn Gly Ala Leu Leu Ser Thr Ala | |
| Rat | Leu Thr Val His Phe Pro Ala Gly Ala Trp Ser Gly Leu Ala Leu Thr Leu Gln Pro Ser Lys Glu Gly Ala Thr Leu Thr Ile Ala | |

|  | | |
|---|---|---|
| Human | Arg Leu Gln Ala Leu Leu Phe Gly Asp Asp His Arg Met Thr Pro Ala .... Leu Leu Leu Leu Leu Pro Arg Ser Glu Pro Ala | |
| Bovine | Gln Leu Gln Ala Leu Leu Phe Gly Ala Asp Ser Arg Cys Phe Thr Arg Lys Thr Pro Ala Leu Leu Leu Leu Pro Ala Arg Ser Ser Ala | |
| Rat | Gln Leu Gln Ala Phe Leu Phe Gly Ser Asp Ser Arg Cys Phe Thr Arg Lys Thr Pro .... Thr Leu Val Leu Leu Pro Pro Thr Gly Pro Thr | |

|  |  |
|---|---|
|  | 250 |
| Human | Pro Leu Pro Ala His Gly Gln Leu Asp Thr Val Pro Phe Pro Pro Pro Arg \| Pro Ser Ala Glu Leu Glu Glu Ser Pro Ser Ala Asp Pro |
| Bovine | Pro Met Pro Ala His Gly Arg Leu Asp Leu Val Pro Phe Pro Gln Pro Arg \| Ala Ser Pro Glu Leu Pro Glu Ala Pro Pro Ser Ala Asp Pro |
| Rat | Pro Gln Pro Ala His Gly Gln Leu Asp Thr Val Pro Phe Pro Gln Pro Gly Leu Ser Leu Glu Pro Glu Asp Leu Pro His Ser Ala Asp Pro |

S-4 like

|  | |
|---|---|
| Human | Phe Leu Glu Thr Leu Thr Arg Leu Thr Arg Ala Leu Arg Val Pro Pro Ala Arg Ala Ser Ala Pro Arg Leu Ala Leu Asp Pro Asp Ala Leu |
| Bovine | Phe Leu Glu Thr Leu Thr Arg Leu Thr Arg Ala Leu Arg Val Ala Leu Ala Gly Pro Pro Ala Arg Ala Ser Pro Pro Arg Leu Ala Leu Asp Pro Gly Ala Leu |
| Rat | Phe Leu Glu Thr Leu Thr Arg Leu Thr Arg Ala Leu Arg Val Ala Leu Ala Arg Gly Pro Leu Thr Arg Ala Ser Asn Thr Arg Leu Ala Leu Asp Pro Gly Ala Leu |

|  |
|---|
| Human | Ala Gly Phe Pro Gln Gly Leu Val Asn Leu Ser Asp Pro Ala Ala Leu Glu Arg Leu Leu Asp Gly Glu Pro Leu Leu Leu Leu Arg |
| Bovine | Ala Gly Phe Pro Gln Gly Leu Val Asn Leu Ser Ser Pro Ala Ala Leu Glu Arg Leu Leu Asp Gly Glu Pro Leu Leu Leu Leu Pro |
| Rat | Ala Ser Phe Pro Gln Gly Leu Val Asn Leu Ser Asn Leu Asp Pro Val Ala Leu Gly Arg Leu Leu Asp Gly Glu Pro Leu Leu Leu Leu Ser |

+ = Cys   X = Leu Rep   ■ = CHO site   − = Tyr   | = Cleavage Site

FIG. 1B

```
             X                                                                           X  +
Human   Pro Thr Ala Ala Thr Thr Gly Asp Pro Ala Pro Leu His Asp Pro Thr Ser Ala Pro Trp Ala Thr Ala Leu Ala Arg Arg Val Ala Ala Glu
Bovine  Pro Thr Ala Ala Thr Thr Gly Val Pro Ala Thr Pro Gln Gly Pro Lys Ser Pro Leu Trp Ala Ala Gly Leu Ala Arg Arg Val Ala Ala Glu
Rat     Pro Ala Ala Ala Thr Thr Val Gly Pro Met Arg Leu His Ser Pro Thr Ser Ala Pro Trp Ala Ala Gly Leu Ala Arg Arg Val Ala Val Glu X                                       X                                               X    +
Human   Leu Gln Ala Ala Ala Ala Glu Leu Pro Gly Leu Pro Pro Ala Pro Thr Ala Pro Leu Leu Ala Arg Leu Leu Ala Leu Cys Pro Gly
Bovine  Leu Gln Ala Ala Ala Val Ala Ala Ala Glu Leu Pro Gly Leu Pro Ala Ala Pro Leu Leu Ala Arg Leu Leu Ala Leu Cys Pro Gly
Rat     Leu Gln Ala Ala Ser Glu Leu Arg Asp Leu Pro Gly Leu Pro Pro Thr Ala Pro Leu Leu Ala Arg Leu Leu Ala Leu Cys Pro Asn N1
                                                                                ┌─────────
Human   Gly Pro Gly Leu Gly Asp Pro Leu Arg Ala Leu Leu Leu Leu Lys Ala Leu Gln Gly Leu Arg Val Glu Trp Arg Gly Arg Asp Pro Arg
Bovine  Asn Pro Asp Ser Pro Gly Pro Gly Pro Leu Arg Ala Leu Leu Leu Leu Lys Ala Leu Gln Gly Leu Arg Ala Gly Leu Trp Arg Gly Arg Gly Arg Glu Arg Ser
Rat     Asp Ser Arg Ser Ala Gly Asp Pro Leu Arg Ala Arg Leu Leu Leu Ala Leu Gln Gly Leu Arg Ala Gly Leu Trp Arg Arg Gly Gly Arg Arg
                                                                                      N1
                                                                 427   ┬
Human   Gly Pro Gly Arg Ala Gln Arg|Ser Ala Gly Ala Thr Ala Ala Ala Ala Asp Gly Pro Cys Ala Leu Arg Glu Leu Ser Val Asp Leu Arg Ala Glu Arg
Bovine  Gly Ser Ala Arg Ala Gln Arg|Ser Ala Gly Ala Gln Ala Gly Pro Cys Ala Leu Arg Glu Leu Ser Val Asp Leu Ser Val Arg Ala Glu Arg
Rat     Gly Arg Ala Gly Arg Ser Gly Lys Gly Thr Gly ............. Thr Asp Gly Leu Cys Ala Leu Arg Glu Leu Ser Val Asp Leu Arg Ala Glu Arg
                                                                                                                    C1
                                                             -        +                         +                              +
Human   Ser Val Leu Ile Pro Glu Thr Tyr Gln Ala Asn Asn Cys Gln Gly Val Cys Gly Trp Pro Gln Ser Asp Arg Asn Pro Arg Tyr Gly Asn His
Bovine  Ser Val Leu_Ile Pro Glu Thr Tyr Gln Ala Asn Asn Cys Gln Gly Ala Cys Gly Trp Pro Gln Ser Asp Arg Asn Pro Arg Tyr Gly Asn His
Rat     Ser Val Leu Ile Pro Glu Thr Tyr Gln Ala Asn Asn Cys Gln Gly Ala Cys Gly Trp Pro Gln Ser Asp Arg Asn Pro Arg Tyr Gly Asn His +     +                  +            -
Human   Val Val Leu Leu Leu Lys Met Gln Ala Arg Gly Ala Ala Leu Ala Arg Pro Pro Cys Cys Val Pro Thr Ala Tyr Ala Gly Lys Leu Leu Ile
Bovine  Val Val Leu Leu Leu Lys Met Gln Ala Arg Gly Ala Ala Leu Ala Arg Pro Pro Cys Cys Val Pro Thr Ala Tyr Thr Gly Lys Leu Leu Leu Ile
Rat     Val Val Leu Leu Leu Lys Met Gln Ala Arg Gly Ala Ala Leu Gly Arg Pro Pro Cys Cys Val Pro Thr Ala Tyr Thr Gly Lys Leu Leu Leu Ile
                                                                                                  +
Human   Ser Leu Ser Glu Glu Arg Ile Ser Ala His His Val Pro Asn Met Val Ala Thr Glu Cys Gly Cys Arg
Bovine  Ser Leu Ser Glu Glu Arg Ile Ser Ala His His Val Pro Asn Met Val Ala Thr Glu Cys Gly Cys Arg
Rat     Ser Leu Ser Glu Glu His Ile Ser Ala His His Val Pro Asn Met Val Ala Thr Glu Cys Gly Cys Arg + = Cys    X = Leu Rep    ■ = CHO site    − = Tyr    | = Cleavage Site
```

FIG.1C

PURIFICATION OF MULLERIAN INHIBITING SUBSTANCE

This invention was made with government support under CA17393 awarded by the National Cancer Institute of the National Institutes of Health. The government has certain rights in the invention.

FIELD OF THE INVENTION

The present invention relates to a process for the purification of biological materials, especially the purification of Müllerian Inhibiting Substance (MIS).

BACKGROUND OF THE INVENTION

The efficient and rapid purification of biological materials such as proteins, nucleic acids or polysaccharides, has been of great interest. Immunoaffinity chromatography is advantageous since, under the proper conditions, purification of 1,000–10,000 fold can be attained. Cf. Harlow, E. et al., *Antibodies: A Laboratory Manual*, Cold Spring Harbor Laboratory (1988).

One protein for which a rapid and efficient purification system is desirable is the biological modifier Müllerian Inhibiting Substance (MIS) produced in vivo by the ovary and testis. MIS is a testicular protein responsible for regression of the anlagen of the female reproductive tract in the fetal urogenital ridge, as well as other differentiative functions such as inhibition of oocyte meiosis and lung surfactant. Previous studies in A431 cells and more recently in fetal lung suggest that MIS is a potent inhibitor of epidermal growth factor receptor autophosphorylation. Cf. Cigarroa et al., Growth Factors 1:79–91 (1989); Coughlin et al., *Mol. and Cell. Endocrinol.* 49:75–86 (1985); and Catlin et al., Metabolism.

Human Müllerian Inhibiting Substance has been cloned and expressed recombinantly (rhMIS) in animal cells as a 140 kDa homodimer (Cate et al., *Cell* 45:685 (1986)). By virtue of carboxy-terminal amino acid homology, MIS is a member of a large gene family that includes TGF-β (Derynck et al., *Nature* 316:701–5 (1985)), inhibin (Mason et al., *Nature* 318:659–63 (1985)), activin (Ling et al., *Nature* 321:779–82 (1986)), Vg1 from Xenopus (Weeks et al., *Cell* 51:861–7 (1987)), the *Drosophila decapentaplegia* protein (Padgett et al., *Nature* 325:81–4 (1987)), and the bone morphogenesis factors (Wozney et al., *Science* 242:1528–34 (1988)).

RhMIS is a 140 kDa glycoprotein composed of two identical subunits which, under disulfide bond reducing conditions, migrates on polyacrylamide gel electrophoresis at an apparent molecular weight of 70 kDa. The protein can be proteolytically cleaved in approximately one hour by exogenous plasmin into two distinct fragments that migrate electrophoretically as 57 kDa and 12.5 kDa moieties with cleavage at residue 427 of the intact 535 amino acid monomer as demonstrated by Pepinsky (Pepinsky et al., *J. Biol. Chem.* 263(35):18961–4 (1988)). Prolonged exposure to plasmin can result in cleavage of MIS at additional sites. In addition, purification of MIS by known techniques can be contaminated by other proteases that also cleave MIS.

MIS has been proposed as a potential growth inhibitor of epithelial human tumors of Müllerian origin such as endometrial, Fallopian tubal, cervical, and certain ovarian neoplasms. Experimental evidence using purified bovine MIS support this hypothesis (U.S. patent application Ser. No. 06/792,233, filed Oct. 19, 1985, now U.S. Pat. No. 5,011,687; Fuller et al., *J. Clin, Endocrinol. Metab.* 54:1051–5 (1982); Fuller et al., *Gynecol. Oncol.* 22:135–48 (1985)). purified rhMIS used in similar in vitro assays, however, demonstrate limited anti-cancer activity (Wallen et al., *Cancer Res.* 49:2005–11 (1989)), Müllerian Inhibiting Substance may be obtained by a variety of different methods. U.S. patent application Ser. No. 06/792,233, filed Oct. 19, 1985, now U.S. Pat. No. 5,011,687, and entitled "Purified Müllerian Inhibiting Substance and Process for Treating Human Ovarian Cancer Cells," describes a process for purifying MIS from testes by using aqueous polar dissociative solutions, separation of DNA and RNA, fractionation by gel filtration chromatography, and isolation of the MIS. U.S. Pat. No. 4,404,188, filed Jul. 29, 1981 and entitled "Purified Müllerian Inhibiting Substance and Method of Purification" describes a process for purifying MIS from testes which comprises treatment with a protease inhibitor, chromatography on ion exchange, chromatography on wheat germ lectin, on concanavalin A and/or on a supported triazinyl dye. U.S. Pat. No. 4,487,833, filed on Mar. 1, 1982 and entitled "Method of Preparing Hybridomas and of Purifying Immunogenic Materials" describes a process for separating MIS using immunoaffinity chromatography. MIS has also been obtained from recombinant DNA techniques as disclosed by Cate (Cate, et al., *Cell* 45:685–698 (1986)). None of the references, however, describe a method of recovering substantially pure MIS which retains an antiproliferative activity or is essentially free of enzymes having proteolytic activity against MIS.

A need, therefore, continues to exist for the development of highly efficient techniques for immunoaffinity chromatography, wherein a biological substance can be isolated from a complex biological mixture without interference from contaminating proteolytic enzymes or other factors that impede MIS antiproliferative activity. In particular, the need exists for an immunoaffinity chromatography method which can isolate and purify MIS so that the isolate will be essentially free from undesired proteolysis or other factors which may alter MIS activity.

SUMMARY OF THE INVENTION

The purification of MIS according to the immunoaffinity purification process of this invention results in a MIS product which is substantially free of enzymes having proteolytic activity or inhibitors of MIS antiproliferative activity. The present invention achieves this goal by providing for a method of purifying MIS comprising (a) binding the MIS to an antibodychromatography matrix, said antibody being specific to MIS, (b) substantially removing contaminating enzymes having MIS proteolytic activity or inhibitors of MIS antiproliferative activity by adding to the matrix an effective amount of an alkali metal halide or an alkaline earth metal halide, and (c) recovering the MIS by eluting with an acid solution having a pH of between about 2.5 and 4.0.

This invention further provides for a composition comprising MIS obtained by (a) binding the MIS to an antibody-chromatography matrix, said antibody being specific to MIS, (b) substantially removing contaminating enzymes having MIS proteolytic activity or inhibitors of MIS antiproliferative activity by adding to the matrix an effective amount of an alkali metal halide or an alkaline earth metal halide, and (c) recovering the MIS by eluting with an acid solution having a pH of between about 2.5 and 4.0.

Also provided by this invention is a composition comprising MIS, wherein said composition is substantially free of enzymes having MIS proteolytic activity or inhibitors of antiproliferative activity of MIS. Such a composition consists essentially of MIS having a molecular weight of 140 kDa or 70 kDa.

BRIEF DESCRIPTION OF THE DRAWING

The present invention will be better understood by reference to the Description of the Preferred Embodiments when taken together with the attached drawing, wherein:

FIGS 1A-1C shows the sequence structure of rhMIS (SEQ. ID. NO: 1) compared to bovine (SEQ. ID. NO: 2) and rat (SEQ. ID. NO: 3) MIS.

DESCRIPTION OF THE PREFERRED EMBODIMENTS

The present invention provides for an improved process for the purification of Müllerian Inhibiting Substance (MIS). This process takes advantage of the specificity of antigen-antibody interactions to recover a product having a substantially pure MIS. Specifically, this invention incorporates the use of immunoaffinity chromatography. The added benefit of this invention is that the immunoaffinity chromatography method is improved such that the recovered MIS product is substantially free of contaminating enzymes having MIS proteolytic activity or inhibitors of antiproliferative activity of MIS.

Immunoaffinity chromatography is a type of chromatography that makes use of a specific affinity between a substance to be isolated, i.e., a ligand, and a molecule that it can specifically bind. The column material is synthesized by covalently coupling a binding molecule to an insoluble matrix. The column material is able to specifically absorb the substance to be isolated from solution. Elution of the product is accomplished by changing the conditions within the column such that the product is released. This procedure either effects the binding site directly or effects the structure of the bound molecule.

If interaction of the ligand to the binder is primarily electrostatic, desorption can be accomplished by a gradient of increasing ionic strength. Ionic strength can be altered by changing pH. Such a change can alter the degree of ionization of charged groups either on the ligand or at the binding site. In desorbing proteins, however, there may be a secondary effect on the protein molecule which results in a conformational change. When binding is due to a hydrophobic interaction, solvents with reduced polarity are effective in desorbing the bound molecule.

In purifying nucleic acids and proteins, desorption has been generally accomplished with the use of chaotropic substances such as $ClO_4^-$, $CF_3COO^-$, $-SCN$, and $CCl_3COO^-$. These substances are useful because they are able to break down very strong interactions.

As described by Pepinsky et al., supra, MIS has been isolated by an immunoaffinity chromatography method. According to this method, MIS is eluted from the matrix by a standard chaotropic salt, NaSCN, and can be recovered at up to 95% purity. Evaluation of MIS when purified according to previously used immunoaffinity methods indicates that the protein has an apparent mass of 70 kDa with fractions also existing as 57 kDa and 12.5 kDa.

As demonstrated by the Example herein, the presence of the 57 kDa and 12.5 kDa fragments are the result of proteolysis or inhibition of the activity of the MIS molecule. Using previously described immunoaffinity methods, contaminating proteolytic enzymes or inhibitors of antiproliferative activity of MIS can be eluted with the pure MIS product. This occurs even though these methods are able to achieve an MIS product of up to 95% purity. The proteolytic enzymes initially cleave the MIS molecule into 57 kDa and 12.5 kDa fragments to activate the molecule. However, further cleavage of the 57 kDa fragment to a 34 kDa fragment and to a 22 kDa fragment occurs. Substances which cleave MIS in this manner include serine proteases, such as plasmin, and endopeptidases. These enzymes are not to be considered as all inclusive or limiting in any manner since other enzymes can also proteolytically cleave MIS and such enzymes can be readily determined by those of ordinary skill in the art.

In order to achieve a substantially pure MIS which will be free of contaminating proteases or inhibitors of antiproliferative activity of MIS, the present invention improves upon the immunoaffinity chromatography method previously employed. This improvement results in a composition which comprises MIS and is substantially free of enzymes having MIS proteolytic activity or inhibitors of antiproliferative activity of MIS.

The immunoaffinity chromatography method of this invention is improved by removing contaminating enzymes having MIS proteolytic activity or inhibitors of antiproliferative activity of MIS from an immunoaffinity chromatography matrix by eluting with an effective amount of an alkali metal halide or an alkaline earth metal halide. The MIS is then recovered by eluting with an acid solution having a pH of between about 2.5 and 4.0. This elution with halide followed by acid is alternatively referred to as sequential salt/acid elution.

The terms "Müllerian Inhibiting Substance" and "MIS", as alternatively used herein, are intended to include compounds and materials which are structurally similar to MIS. Examples of such included substances and materials are salts, derivatives, and aglycone forms of MIS. Additionally, the present invention is intended to include mutant forms of MIS which have substantially the same biological activity as MIS. Examples of such mutant forms would be MIS molecules carrying at least one deletion, insertion, or alteration in amino acid sequence. MIS may be obtained from any mammalian source or, as indicated above, from non-mammalian sources through the use of recombinant DNA technology, or from the chemical synthesis of the MIS protein. The purification method of this invention is preferably directed toward the recovery of recombinant human MIS.

The term "protein" is meant to include both synthetic and naturally-occurring amino acid sequences derivable from the naturally occurring amino acid sequence of MIS. The protein is said to be "derivable from the naturally-occurring amino acid sequence of MIS" if it can be obtained by fragmenting the naturally-occurring chosen sequence of MIS, or if it can be synthesized based upon a knowledge of the sequence of the naturally occurring amino acid sequence or of the genetic material (DNA or RNA) which encodes this sequence.

The invention further pertains to polypeptides that, in addition to the chosen sequence, may contain or lack one or more amino acids that may not be present in the naturally-occurring sequence, wherein such polypeptides are functionally similar to or possess antagonist activity to the chosen polypeptide. Such polypeptides for the present invention, are termed "functional derivatives," provided that they demonstrate activity which is substantially similar to or antagonistic to that of MIS.

The MIS composition may be in the form of the free amines (on the N-terminus), or acid-addition salts thereof. Common acid solution salts are hydro halic acid salts, i.e., HBr, HI, or more preferably, HCl.

The purified MIS of this invention can be obtained in solution at up to 95% purity or greater. While the percent purity is comparable to other immunoaffinity purification processes, the MIS composition of this invention is substantially free of contaminating proteolytic enzymes or inhibitors of MIS antiproliferative activity.

For purposes of this invention, purified MIS is considered to be a MIS composition which is substantially free of contaminating proteolytic enzymes or inhibitors of MIS antiproliferative activity regardless of percent purity. The composition is considered to be substantially free of proteolytic enzymes if gel electrophoresis of the purified MIS product indicates a protein having a molecular weight of 140 kDa or 70 kDa. Gel electrophoresis of such a product will not show time dependent proteolytic fragments which are degradation products of MIS. For example the 57 kDa, 12.5 kDa, 34 kDa and 22 kDa degradation fragments of MIS further described herein will not be readily discernable by standard gel electrophoresis methods.

The MIS composition will be considered to be substantially free of inhibitors of MIS antiproliferative activity if the MI blocks proliferation of certain tumor cells. Examples of such tumor cells are included herein and in U.S. patent application Ser. No. 07/683,966, now abandoned, and which is fully incorporated herein by reference. These examples include tumors selected from the group consisting of vulvar epidermoid carcinoma, endometrical adenocarcenoma, cervical carcenoma, endometrial adenocacenoma, ovarian adenoracenoma, and other ocular melanoma. The determination of antiproliferation activity of these tumors as well as any other tumor can be achieved by any of the procedures described herein and in U.S. patent application Ser. No. 07/683,966, now abandoned.

In order to obtain MIS which is substantially free of proteolytic enzymes or inhibitors of MIS antiproliferative activity, the contaminants are separated from the MIS using immunoaffinity chromatography. Separation occurs by eluting the enzymes or inhibitors with an alkali metal halide or an alkaline earth metal halide. Such a compound will generally be in solution and an effective amount of halide will be between about 0.1M and 2.0M. As alkali metals, the ions of lithium, sodium and potassium are preferred with sodium being most preferable. As alkaline earth metals, the ions of magnesium and calcium are preferred. As halides, the ions of fluorine, chlorine, bromine and iodine are preferred with chlorine being most preferable. When eluting with sodium chloride, a solution of between about 0.1 and 2.0M is preferred. The concentration of halide can also be varied as elution progresses if desired. This can be accomplished by increasing molar concentration of halide in a stepwise fashion. It is preferred that each step be altered after about 0.1–2.0 bed volumes of solution have contacted the chromatography matrix, although such steps can be further modified as desired.

The halide can also be accompanied in solution with an effective amount of a chelating agent. These agents are capable of binding metal ions which can inactivate enzymes that require the metal ions for activity. Such agents include the compounds ethylenediamine tetraacetate (EDTA), and ethylenebis(oxyethylenenitrilo)-tetraacetic acid (EGTA). Chelants can be effectively added in a range of between 0.1 and 50 mM.

After the contaminating proteolytic enzymes or inhibitors of MIS antiproliferative activity have been separated, the MIS can be recovered by eluting with an acid solution having a pH of between about 2.0 and 4.0. Although dilutions of strong acids such as HCl can be used, organic acids are preferred because of their relatively mild acid strength. For example, the use of acid amines and imines can be employed as well as monocarboxylic, dicarboxylic and tricarboxylic acids. Preferred as monocarboxylic acids are acetic, propionic and butyric acid. Preferred as dicarboxylic acids are succinic, fumaric and malic acid. Preferred as a tricarboxylic acid is citric acid. Preferred among the amines are the acidic amino acids such as aspartic and glutamic acid. The pH of the acid solution can also be incrementally varied as in the application of the halide.

After the purified MIS product has been eluted, it is preferable to neutralize the product to a pH of between 6.8 and 7.6 to guard against acid hydrolysis. This can be accomplished by various hydroxide compounds such as NaOH or NH₄OH or by various buffers which can quickly achieve neutralization of the product in the desired pH range. These hydroxide compounds are not to be considered as all inclusive as those of ordinary skill in the art will appreciate.

Preparation of an immunoaffinity chromatography column is well known in the art as demonstrated by Harlow et al.. *Antibodies: A Laboratory Manual*, Cold Spring Harbor Laboratory, 1988. For purposes of this invention it is preferable that the chromatography column have a matrix which can be coupled to an antibody specific to MIS. The matrix will generally be solid phase support which binds antibody easily and is commercially available. For example, Protein A can be used as the chromatography matrix. This matrix specifically binds to the Fc domain of antibodies and, after the antibody is bound, the interaction is stabilized by cross-linking with a bifunctional coupling reagent. In preparing a protein A bead-antibody column, any bifunctional coupling reagent can be used. The use of methylpimelimidate is generally preferred.

Another method of preparing an immunoaffinity column couples the antibody to an activated bead. The beads are activated chemically to contain reactive groups. Examples of beads which can be used in this method are agarose beads, cross-linked agarose beads, polyacrylamide beads, copolymers of polyacrylamide and agarose, and polyacrylic beads. Compounds which are generally used to activate the beads are carbonyldiimidoxole, cyanogen bromide, glutaraldehyde, hydroxysuccinimide, and tosyl chloride. After the beads are activated, they are then mixed and coupled with purified antibodies.

Yet another method of coupling antibodies to beads is to activate the antibody first. Purified antibodies can be activated by treating with a bifunctional reagent, one group binding to an appropriate group on the antibody and the other remaining free to bind to the matrix. Reagents which can generally be used for indirect coupling are the water-soluble carbodiimides such as dicyclohexylcarbodiimide (DCCD), 1-ethyl-3-(3-dimethylaminopropyl)-carbodiimide HCl (EDAC or DECI), or 1-cyclohexyl-3-(2-morpholinoethyl)-carbodiimide-metho-p-toluene-sulfonate (CMIC or CMLI); the condensing agents for peptide synthesis such as N-ethoxycarbonyl- 2-ethoxy-1,2-dihydroquinoline (EEDQ); glutaraldehyde; or periodate. After the antibodies are activated, they are bound to beads.

Having now generally described this invention, the same will be better understood by reference to a certain, specific example which is included herein for purposes of illustration only and is not intended to be limiting of the invention, unless specified.

EXAMPLE

I. Materials and Methods

A. RhMIS Purification

Recombinant human MIS (rhMIS) was purified from the conditioned media of Chinese hamster ovary (CHO) cells, transfected with a linear construct of the human rhMIS gene and the DHFR gene, amplified by 30M Methotrexate selection, grown to confluence in four liter bioreactors on stainless steel coils as described by Epstein (Epstein et al., *In Vitro Cell. and Devel. Biol* 25(2):213–6 (1989)) or modified roller bottles in alpha-Modified Eagle's Medium (α-MEM-), supplemented with 5% female fetal calf serum (FFCS), 10 mg/ml Amikacin, 1.3 g/l -glutamine, 2.0 g/l d-glucose, and 0.1 g/l sodium pyruvate, in the absence of nucleosides. The medium was collected every 3–4 days, and stored at −20° C. Media were thawed and filtered through Whatman #4 filter paper to remove debris, concentrated 20x an a Minitan (Millipore) with a 30 kDa exclusion ultrafilter, and stored at −70° C., until purification. A 5 ml immunoaffinity column was constructed using approximately 50 mg of a Protein A-Sepharose (BioRad) purified monoclonal anti-human rhMIS antibody [6E11], as described by Hudson (Hudson et al., *J. Clin. Endocrinol.* 70:16–22 (1990)), and covalently attached to Affigel-10 agarose resin (BioRad), per the manufacturer's instructions (approximately 80% coupling efficiency). The column was equilibrated with 100 mls of 20 mM HEPES, pH 7.4, and 200 ml of the concentrated media loaded at 1 column volume/hour at 4° C. After loading, the column was washed with 20 mM HEPES, pH 7.4, until the absorbance at 280 nm returned to baseline (60–100 mls).

Elution of rhMIS bound to this column was achieved using 2.0M sodium thiocyanate (NaSCN); or 1M Acetic acid, 20 mM HEPES, pH 3.0, with and without a pre-elution step containing 0.5M NaCl, 1 mM EDTA, 0.001% NP-40, 20 mM HEPES, pH 7.4. The majority of the rhMIS protein eluted in a single 2 ml fraction, which was immediately desalted by G-25 size exclusion chromatography in 0.02M HEPES, 0.15M NaCl, 10% glucose, pH 7.4, in the case of chaotropic salt elution, or immediately neutralized with either NaOH or NH$_4$OH to a pH between 7.0 and 7.4, when eluted with acid. Depending on the initial pH of the fraction and technique of neutralization, dilutional effects ranged from 10–50%. The resultant rhMIS was examined for total protein according to the method of Bradford (Bradford, Anal. Biochem. 72:248–54 (1976)), for rhMIS concentrations by enzyme-linked immunosorbant assay [ELISA] according to the method of Hudson (Hudson et ( al., .J. Clin. Endocrinol 70:16–22 (1990)), on polyacrylamide gel electrophoresis [PAGE] according to the method of Weber (Weber et al., J. Biol. Chem. 244(16):4406–12 (1969)), in Western blot analysis using polyclonal (anti-homo, and anti-N- and C-terminal peptide) antibodies to rhMIS according to the method of Towbin (Towbin et al., PNAS 76:4350–4 (1979)), for NH$_2$-terminal sequencing, in organ culture bioassay for Müllerian duct regression, and in tumor antiproliferative assays.

B. RhMIS Bioassay

The standard organ culture bioassay for MIS was performed as described by Donahoe (Donahoe et al., *Biol. Reprod.* 16:238–43 (1977)). Briefly, 14½ day female fetal rat urogenital ridges were placed on agar coated stainless steel grids above fortified CMRL 1066 media to which test preparations were added at concentrations less than 20% (v/v). After incubation for 72 hours in humidified 5% $CO_2$ at 37° C., the specimens were aligned, fixed in 15% formalin, embedded in paraffin, cut in 8 mm cross sections from cephalic to caudal, and then stained with hematoxylin and eosin. The sections were then graded from 0 (no regression) to 5 (complete regression). Female fetal calf serum was used to avoid contamination of the assay with bovine MIS. This change required the addition of $10^{-9}$M testosterone to aid the expression of the Wolffian duct for morphologic comparison according to the method of Ikawa (Ikawa et al., *J. Ped. Surg.* 17:453 (1982)).

C. RhMIS ELISA

The enzyme linked immunosorbent assay (ELISA), employing anti-rhMIS monoclonal and polyclonal antibodies, was used to measure the rhMIS content in all preparations. This assay, described by Hudson (Hudson et al., *J. Clin. Endocrinol* 70:16–22 (1990)), detects intact rhMIS with a sensitivity of 1–2 ng/ml, with minimal cross reactivity with N- and C-terminal fragments of rhMIS, and no recognition of Transforming Growth Factor β (another member of the same gene family as MIS), the humor gonadotropin, follicle stimulating hormone, and luteinizing hormone, or proteins contained in conditional medium of wild type CHO cells.

D. Antiproliferative Assays

Immunoaffinity purified rhMIS was assayed for anti-tumor activity as described by U.S. patent application Ser. No. 07/683,966, now abandoned, using a double layer agarose colony inhibition assay as described by Fuller (Fuller et al., *Gynecol. Oncol* 22:135–48 (1985)). Human cancer cell lines, including A431, Hep3b, HEC1, OM431, OM467, and RT4, were plated on an underlayer of 0.6% agarose in α-MEM+ and FFCS. After addition of rhMIS or vehicle control, plates were incubated for 14 days at 37° C., 5% $CO_2$, and colonies of more than 30 cells were counted. A liquid media colony inhibition assay that requires fewer cells and 5–7 day incubation period was also used. Colonies were counted using a computer aided automated program.

E. RhMIS Antibody Preparations

Rabbit polyclonal antiserum against 140 kDa homo rhMIS (MGH-1), electroeluted from polyacrylamide gels according to the method of Hunkapillar (Hunkapillar et al., *Meth. Enzymol.* 91.486 (1983)), was prepared as previously described by Hudson (Hudson et al., *J. Clin. Endocrinol.* 70:16–22 (1990)). Epitope specific rabbit polyclonal antibodies were raised to regions of the rhMIS molecule NH$_2$-terminal (MGH-N1) or COOH-terminal (MGH-Cl) to the monobasic consensus cleavage site at position 427. Synthetic peptides corresponding to residues 411–424 and 471–482 in rhMIS, respectively, constructed from the predicted amino acid sequence of human rhMIS (FIGS. 1A–1C) were used as antigens. These sequences were chosen for their conserved homology among human, bovine and rat MIS, their differences from other members of the supergene family, and their antigenicity and surface probability (i.e., the likelihood that a specific region will present itself for antigen recognition), as predicted by the sequence analysis software package of the Genetics Computer Group at the University of Wisconsin version 5]. This program measures hydrophobicity as outlined by Chou and Fasman (Chou et al., *Advances in Enzymology* 47:45–147 (1978)), and antigenicity and surface probability by the method of Wolf et al. (Wolf et al., *Comput. Appl. Biosci.* 4(1):187–91 (1988)).

New Zealand white rabbits were injected in the popliteal lymph nodes with 25–50 μg of relevant peptide, conjugated 1:1 with keyhole limpet hemocyanin complete Freund's adjuvant. These animals were boosted by subcutaneous injection in the back, 4–6 weeks later, with 20–30 μg of unconjugated peptide in incomplete Freund's adjuvant. Animals were bled through an ear vein and the serum stored at −20° C. Polyclonal antiserum was purified by 50% $(NH_4)_2SO_4$ precipitation, followed by Protein A-Sepharose chromatography. The monoclonal antibody 6E11 was raised according to the method of Kohler (Kohler, G, *Immunol. Methods* 2:285–98 (1981)) and purified by Protein-A Sepharose affinity chromatography. Control antisera were purchased from DAKO.

F. Temperature, pH, and Storage Effects on rhMIS Preparations

Immunoaffinity purified rhMIS was sterile filtered using a Millex-GV 0.22 μm filter unit (MILLIPORE), divided into 200 μl aliquots and incubated at −80° C., −20° C., +4° C., +25° C., +36° .C, and +70° C. to determine temperature stability of the rhMIS molecule. To observe the effects of storage at various temperatures, aliquots of rhMIS at 3, 7, 11, 14 and 31 days, were subjected to Bradford protein assay (Bradford, M.M., *Anal. Biochem* 72:248–54 (1976)), ELISA, polyacrylamide gel electrophoresis in sodium dodecyl sulfate (SDS-PAGE), western blot analysis, organ culture bioassay, and selected aminoterminal analysis. Additionally, preparations of rhMIS were stored at pH 3.0 for 1, 2, and 4 hours, and 2, 3, 5, and 8 days at +4° C. and +36° C. For comparison, a non-cleavable mutant of rhMIS, produced by site-directed mutagenesis of $Arg^{427}$ to $Thr^{427}$, was tested after a days storage at 37° C.

G. Enzyme Treatments

RhMIS was treated with plasmin for 2 hours, as described by Pepinsky et al., supra, for 1, 3, and 7 days, and with 0.1% trypsin for 1 hr at 4° C. The reactions were quenched with 10% fetal bovine serum. The effect of protease inhibitors was assessed with phenylmethyl sulfonyl fluoride, 0.1 mM; soybean trypsin inhibitor, 1 mM; leupeptin, 1 mM; pepstatin, 1 mM; all used together as a mixture, or tosyllysine chloromethyl ketone, 1 mM, alone. Additionally, rhMIS was assayed for intrinsic enzyme activities. Protease activity was determined using azocasein (2 mg/ml in 0.05M Tris-Cl, pH 8.5) as a substrate (Worthington manual 1970). 0.9 ml was brought to 37° C. in a water bath prior to addition of 0.1 ml of enzyme (1–20 mg/ml Subtilisin) or rhMIS. The reaction was allowed to proceed for 15 minutes at 37° C., and 0.25 ml 70% perchloric acid was added. The samples were placed on ice for 15 minutes, then centrifuged at 4° C. to pellet the precipitate. Absorbance of the supernatant was measured spectrophotometrically at 405 nm. Acid and alkaline phosphatase activities were examined with Sigma chemical kit #104, which measures the ability to hydrolyze p-nitrophenyl phosphate.

H. Sequencing

Acid eluted, immunoaffinity purified rhMIS was submitted as "homo" rhMIS for $NH_2$-terminal sequencing. A similar preparation was heated to 37° C. for 8 days to allow cleavage of 70 kDa intact rhMIS to 57 kDa, 34 kDa, 22 kDa, and 12.5 kDa as determined by SDS-PAGE. These bands were then electroeluted from the gel, according to the method of Hunkapillar (Hunkapillar et al.. *Meth. Enzymol.* 91:486 (1983)), and analyzed for N-terminal sequence. The sequential salt/acid eluted rhMIS was similarly submitted for sequence analysis except the cleavage was done by exogenous plasmin. The 34 kDa fragment, which required concentration by lyophilization prior to PAGE, was electrophoretically transferred to an Immobilon PVDF membrane (Millipore), stained, and sequenced. Edman degradation was performed on a model 470A Applied Biosystems gas phase sequencer; PTH-amino acids were analyzed on an on-line microbore HPLC (ABI model 120A).

I. Electrophoresis

Polyacrylamide gel electrophoresis (PAGE) was carried out by the procedure of Laemmli (Laemmli, *Nature* 227:680–5 (1970)), as follows: 10 or 15% homogeneous gels were prepared in Hoefer gel casting stands to produce 160×160×1.5 mm slabs, and gels run at 150V, 30 mA constant current. Proteins in the gels were stained with 0.1% Coomassie Brilliant Blue R250 (Sigma) in 50% methanol, 10% acetic acid for 1 hour before destaining in 50% methanol, 10% acetic acid. As appropriate, samples were reduced using 0.75 M 2-mercaptoethanol with heating to boiling for 1o min. Molecular weight standards were obtained from BioRad.

For western analysis, gels were incubated in transfer buffer (3 g Tris, 14.4 g/l glycine) prior to electrophoretic transfer to nitrocellulose or Immobilon-PVDF (Milligen Corp.) sheets according to the BioRad technical bulletin no. 83-0050. After the transfer, the sheets were used directly for microsequencing, or blocked by incubation with 30 mg/ml bovine serum albumin for 30 minutes at room temperature, with shaking. Thereafter, the blots were incubated with 1:500 to 1:1000 fold dilutions of rabbit polyclonal anti-rhMIS or anti-rhMIS peptide antisera for 2 hrs, then washed with 0.05M Tris-Cl, 0.15M NaCl prior to addition of a 1:1000 dilution of goal anti-rabbit horseradish peroxidase conjugate (BioRad). Antibody complexes were visualized by the addition of BioRad color reagent for 1–4 minutes, prior to quenching the reaction with water.

For microsequencing, proteins were transferred according to the BioRad technical bulletin No. 83-0050 into Immobilon PVDF sheets and stained with Coomassie blue as described above for gels except that acetic acid was omitted.

J. Labelling of RhMIS

RhMIS, prepared by either sequential salt/acid or acid only elution, was iodinated by the chloramine T method of Hunter (Hunter, *Proc. Soc. Exp. Biol. Med.* 133(3):989–92 (1970)). Briefly, to 0.5 ml (0.3 mg/ml) of rhMIS, 10 μl of $Na^{125}I$ (Amersham) and 10 μl of chloramine T (2.5 mg/ml; Sigma) were added. After 90 seconds, the reaction was quenched with 25 μl of $NaHSO_3$ (7.6 mg/ml). The mixture was desalted on a 10 ml Sephadex G-25 column, equilibrated in 20 mM HEPES, pH 7.4.

Biotinylation (Pierce Chemical Co. Bulletin No.21335) was carried out using water soluble N-hydroxysuccinimide-long chain alkyl-biolin. 0.5 ml of rhMIS (0.3 mg/ml) was dialyzed overnight at 4° C. vs PBS. 5 μl of 4.5 mg/ml NHS-LC-Biotin was added and the mixture incubated at 4° C. with gentle agitation for 4 hours, then dialyzed overnight at 4° C. vs PBS.

Fluorescent rhMIS was prepared with fluorescein isothiocyanate [FITC] according to the method of Johnson (Johnson et al., J. Biol. Chem. 257(10):5632-6 (1982)), as follows. Approximately 200 μg of rhMIS was dialyzed, overnight at 4° C., vs 2×4 l 0.05M TRIS, pH 8.8. One tenth volume of fluorescein isothiocyanate (FITC) in TRIS 8.8 was added (50Å FITC/500Å MIS), and the reaction allowed to proceed for 30 minutes at 4° C. The reaction mixture was desalted with a 10 ml Sephadex G-25 column equilibrated in PBS. Protein was monitored at $A_{280}$ and fluorescence at $A_{493}$. The protein and fluorescence peaks co-eluted with the void volume.

II. RESULTS

Immunoaffinity purified rhMIS migrates on SIS-PAGE under reducing conditions, at an apparent molecular weight of 70 kDa regardless of the method of elution. A 57 kDa minor band was also seen. These two bands, which represented approximately 90% of the Coomassie Brilliant Blue stained protein on reducing gels, as well as the 140 kDa dimeric species in nonreducing gels, bind polyclonal antibody against rhMIS dimer. RhHIS subjected to PAGE without SDS, or under conditions of reverse polarity, failed to enter the gel. The acid elution of rhMIS from the immunoaffinity column resulted in higher yields and greater purity than did chaotropic elution (Table 1). Sequential salt/acid elution resulted in rhMIS being substantially free from enzymes having MIS proteolytic activity.

TABLE 1

| SAMPLE | PROTEIN CONCEN-TRATION | MIS (ELISA) | % MIS | FOLD PURITY | YIELD |
|---|---|---|---|---|---|
| MEDIA | 1.75 mg/ml | 3.43 +/− 1.47 μg/ml | 0.196 | 1 | 100 |
| IAP (S/A) n = 8 | 0.388 mg/ml | 297 μg/ml | 77 | 392 | 4.4 |
| IAP (Acid) n = 14 | 1.06 +/− 0.6 mg/ml | 964 +/− 660 μg/ml | 91 | 464 | 13.8 |
| IAP (SCN) n = 13 | 0.87 +/− 0.3 mg/ml | 620 +/− 480 μg/ml | 71 | 362 | 11.3 |

RhMIS prepared by single step elution with either chaotropic salt or acid alone undergoes a time and temperature dependent cleavage that is blocked by proteolytic inhibitors. RhMIS prepared by sequential salt and acid elution does not undergo endogenous proteolytic processing. The major species after cleavage are monomers of 57 kDa and 12.5 kDa, consistent with cleavage at residue 427. Amino acid sequence of freshly purified rhMIS yields the known amino terminal sequence LeuArgAlaGluGluProAlaValGlyThr (SEQ. ID. NO: 4). After cleavage, a second sequence AlaAlaGlyAlaThrAlaAlaAspGlyPro (SEQ. ID. NO: 5) is found which, except for the first amino acid, matches the carboxy-terminal sequence of rhMIS beginning at residue 428.

The 34 kDa moiety, seen with prolonged incubation of acid only eluted rhMIS at +36° C., was sequenced successfully after lyophilization and electrophoretic transfer to PVDF membrane. This species yielded the NH2-terminal sequence of rhMIS (i.e., LeuArgAlaGlu-GluProAlaValGlyThr, SEQ. ID. NO: 4), indicative of a second processing event N-terminal to that at residue 427. Sequential salt/acid eluted material showed this same band and the 57 and 12.5 kDa bands after treatment with exogenous plasmin. Occasionally, an additional fragment with apparent molecular weight of 22 kDa was seen, but this fragment was not sequenced. Furthermore, the polyclonal antibodies raised to peptides constructed from the predicted amino acid sequence, both C-terminal or N-terminal to the monobasic protease cleavage site (residue 427), recognized 140 kDa "homo" rhMIS on western blots. Antibody MGH-N1, raised to the peptide corresponding to residues 411–424, recognized only 70 kDa and 57 kDa species. C-terminal anti-peptide (471–482) antibody MGH-C1 recognized the 12.5 kDa species seen in 36° C. treated samples, as well as uncleaved, reduced rhMIS (70 kDa). Additionally, MGH-C1 weakly recognized cleaved N-terminal 57 kDa rhMIS, indicating possible cross-reactivity, due to the polyclonal nature of the antibody which was raised to KLH conjugated peptide. A polyclonal antibody, termed MGH-1, which was raised to intact immunoaffinity purified rhMIS, recognized the 140 kDa, 70 kDa, and 57 kDa species, as well as the 34 kDa and 22 kDa fragments. These antibodies recognized similar bands on western blots of a less homogeneous, dye affinity purified rhMIS.

Although protein levels measured by Bradford analysis do not change with the time of incubation, the ELISA values decrease as cleavage increases. In spite of the proteolytic cleavage, however, rhMIS remains biologically active even if the protein is stored at neutral pH for 1 month at temperatures up to 36° C. RhMIS activity is lost, however, by heating to 70° C. for 4 days, by treatment with 0.1% Trypsin, and by storage for greater than 24 hours in acid (1M HAc), at 36° C. Acid storage at 4° C. loses activity more slowly (30–50% at 8 days).

Iodinated, biotinylated, and fluoresceinated rhMIS were all active in the organ culture bioassay at approximately 50% of their prelabelling levels. FITC labelled rhMIS was immunoreactive in the ELISA at only 20% of its original level, while iodinated or biotinylated material retained virtually all of its immunoreactivity. All labelled preparations showed the characteristic rhMIS bands on PAGE.

To determine if rhMIS acts as an enzyme, i.e., an auto protease, it was assayed in a standard subtilisin az )casein assay. RhMIS eluted with acid alone showed subtilisin-like activity of 1.3 μg/mg rhMIS, in the azocasein assay. Sequential salt/acid eluted material had no activity in this assay, indicating that the copurifying protease had been effectively separated from rhMIS. By effectively separated, it is to be understood that the protease had been actually removed or inactivated such that it was no longer effective in cleaving the MIS molecule.

Sequential salt/acid eluted rhMIS, treated with plasmin for 2 and 24 hours, yielded the predicted cleavage at $Arg^{427}$, to generate the 57 kDa and 22.5 kDa moieties; these were also seen after prolonged processing of acid-only eluted rhMIS at 36° C. Reaction of sequential salt/acid eluted rhMIS with plasmin for longer periods (3-7 days) shows that after the initial cleavage, the 57 kDa fragment is further cleaved to the 34 kDa species. This species was also observed after prolonged storage at 36° C. of rhMIS purified without the salt pre-elution step. The 34 kDa moiety, generated from the sequential salt/acid eluted rhMIS by prolonged plasmin treatment, was sequenced to yield the NH$_2$-terminal sequence of MIS, thus indicating a secondary cleavage event to yield the 34kDa fragment.

To address the frustratingly variable or absent response of rhMIS purified without the salt elution step in antiproliferative assays reported by Wallen (Wallen et al., Cancer Res. 49:2005-11 (1989)), the further refined rhMIS preparations (sequential salt/acid eluted MIS) were tested in similar assays. The rhMIS produced following the salt pre-elution step retains all previous activities, and further is consistently inhibitory in colony inhibition, cell cycle, and subrenal capsule protocols. Examination of the proteins eluted by the 0.5M salt wash shows 3 low molecular weight bands on reducing gels, which were not recognized by either MGH-1 (polyclonal anti-"homo"rhMIS) or MGH-C1 (polyclonal anti-C-terminal peptide).

Analysis of the sequence structure of rhMIS (FIGS. 1A-1C, SEQ. ID. NO: 1) revealed a string of nine leucine repeats beginning at residue 350, followed by a basic region immediately preceding the Arg$^{427}$ cleavage site. This string of repeats strongly resembles a leucine zipper as reported by Vinson (Vinson et al., Science 246(4932):911-6 (1989)). Additionally, there are several other leucine rich regions upstream of this zipper, probably representing the hydrophobic core of the molecule. One of the stretches, beginning at Leu$^{266}$, shows similarities to the S4 domain of the gated ion channels (Tempel et al., Nature 332:837 (1988)). There was also present at positions 194-8, the sequence Arg Gly Glu Asp Ser (SEQ. ID. NO. 6), strikingly similar to the Arg Gly Asp Ser (SEQ. ID. NO. 7) site for fibronectin binding, which may account for the recognition of a basement membrane binding site for rhMIS by antibody to NH$_2$-terminal rhMIS peptide.

Having now fully described this invention, it will be appreciated by those skilled in the art that the same can be performed within a wide range of equivalent parameters of composition and conditions without departing from the spirit or scope of the invention or of any embodiment thereof.

---

What is claimed is:

1. A method of purifying recombinant MIS from host cells capable of expressing recombinant MIS comprising
   (a) binding the recombinant MIS to an antibody-chromatography matrix, said antibody being specific to MIS,
   (b) substantially removing contaminating enzymes having MIS proteolytic activity or inhibitors of MIS antiproliferative activity by adding to the matrix an effective amount of an alkali metal halide solution wherein said solution contains an effective amount of chelating agent, and
   (c) recovering the recombinant MIS by eluting with an acid solution having a pH of between about 2.5 and 4.0.

2. The method of claim 1, further comprising neutralizing the recovered MIS to a pH of between about 6.8 and 7.6.

3. The method of claim 1, wherein the alkali metal halide solution is between about 0.1M and 2.0 M.

4. The method of claim 1, wherein the alkali metal halide is sodium chloride.

5. The method of claim 1, wherein the acid is acetic acid.

6. The method of claim 3, wherein the alkali metal halide solution is between about 0.5M and 2.0M.

7. The method of claim 6, wherein the alkali metal halide solution is about 0.5M.

8. The method of claim 1, wherein said host cells are Chinese hamster ovary cells.

9. The method of claim 1, wherein said chelating agent is EDTA.

* * * * *

UNITED STATES PATENT AND TRADEMARK OFFICE
CERTIFICATE OF CORRECTION

PATENT NO. : 5,310,880
DATED : May 10, 1994
INVENTOR(S) : Patricia K. Donahoe et al.

It is certified that error appears in the above-indentified patent and that said Letters Patent is hereby corrected as shown below:

On the title page, item [75] Inventors: the third inventor's last name "MacLaughkin" should read --MacLaughlin--; and after inventor Richard C. Ragin, the inventor's misspelled hometown address "Brayton" should read --Brighton--.

Signed and Sealed this

First Day of November, 1994

Attest:

Attesting Officer

BRUCE LEHMAN

Commissioner of Patents and Trademarks

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 560 amino acids
        ( B ) TYPE: amino acid
        ( D ) TOPOLOGY: linear ( i i ) MOLECULE TYPE: protein ( x i ) SEQUENCE DESCRIPTION: SEQ ID NO:1:

```
Met Arg Asp Leu Pro Leu Thr Ser Leu Ala Leu Val Leu Ser Ala Leu
 1               5                  10                 15

Gly Ala Leu Leu Gly Thr Glu Ala Leu Arg Ala Glu Glu Pro Ala Val
            20                  25                 30

Gly Thr Ser Gly Leu Ile Phe Arg Glu Asp Leu Asp Trp Pro Pro Gly
            35                  40                 45

Ile Pro Gln Glu Pro Leu Cys Leu Val Ala Leu Gly Gly Asp Ser Asn
    50                  55                 60

Gly Ser Ser Ser Pro Leu Arg Val Val Gly Ala Leu Ser Ala Tyr Glu
 65                 70                 75                 80

Gln Ala Phe Leu Gly Ala Val Gln Arg Ala Arg Trp Gly Pro Arg Asp
             85                  90                 95

Leu Ala Thr Phe Gly Val Cys Asn Thr Gly Asp Arg Gln Ala Ala Leu
            100                105                110

Pro Ser Leu Arg Arg Leu Gly Ala Trp Leu Arg Asp Pro Gly Gly Gln
            115                120                125

Arg Leu Val Val Leu His Leu Glu Glu Val Thr Trp Glu Pro Thr Pro
    130                 135                140

Ser Leu Arg Phe Gln Glu Pro Pro Pro Gly Gly Ala Gly Pro Pro Glu
145                 150                155                160

Leu Ala Leu Leu Val Leu Tyr Pro Gly Pro Gly Pro Glu Val Thr Val
            165                170                175
```

| | | | | | | | | | | | | | |
|---|---|---|---|---|---|---|---|---|---|---|---|---|---|
|Thr|Arg|Ala|Gly 180|Leu|Pro|Gly|Ala|Gln 185|Ser|Leu|Cys|Pro|Ser Arg Asp 190|
|Thr|Arg|Tyr 195|Leu|Val|Leu|Ala|Val 200|Asp|Arg|Pro|Ala|Gly 205|Ala Trp Arg|
|Gly|Ser 210|Gly|Leu|Ala|Leu|Thr 215|Leu|Gln|Pro|Arg|Gly 220|Glu|Asp Ser Arg|
|Leu 225|Ser|Thr|Ala|Arg|Leu 230|Gln|Ala|Leu|Leu|Phe 235|Gly|Asp|Asp His Arg 240|
|Cys|Phe|Thr|Arg|Met 245|Thr|Pro|Ala|Leu|Leu 250|Leu|Leu|Pro|Arg Ser Glu 255|
|Pro|Ala|Pro|Leu 260|Pro|Ala|His|Gly|Gln 265|Leu|Asp|Thr|Val 270|Pro Phe Pro|
|Pro|Pro|Arg 275|Pro|Ser|Ala|Glu|Leu 280|Glu|Glu|Ser|Pro|Pro 285|Ser Ala Asp|
|Pro|Phe|Leu|Glu 290|Thr|Leu|Thr 295|Arg|Leu|Val|Arg|Ala 300|Leu|Arg Val Pro|
|Pro 305|Ala|Arg|Ala|Ser|Ala 310|Pro|Arg|Leu|Ala|Leu 315|Asp|Pro|Asp Ala Leu 320|
|Ala|Gly|Phe|Pro|Gln 325|Gly|Leu|Val|Asn|Leu 330|Ser|Asp|Pro|Ala Ala Leu 335|
|Glu|Arg|Leu|Leu 340|Asp|Gly|Glu|Glu|Pro 345|Leu|Leu|Leu|Leu 350|Leu Arg Pro|
|Thr|Ala|Ala|Thr 355|Thr|Gly|Asp|Pro|Ala 360|Pro|Leu|His|Asp 365|Pro Thr Ser|
|Ala|Pro|Trp 370|Ala|Thr|Ala|Leu|Ala 375|Arg|Arg|Val|Ala|Ala 380|Glu Leu Gln|
|Ala 385|Ala|Ala|Ala|Glu|Leu 390|Arg|Ser|Leu|Pro|Gly 395|Leu|Pro|Pro Ala Thr 400|
|Ala|Pro|Leu|Leu|Ala 405|Arg|Leu|Leu|Ala|Leu 410|Cys|Pro|Gly|Gly Pro Gly 415|
|Gly|Leu|Gly|Asp 420|Pro|Leu|Arg|Ala|Leu 425|Leu|Leu|Leu|Lys 430|Ala Leu Gln|
|Gly|Leu|Arg 435|Val|Glu|Trp|Arg|Gly 440|Arg|Asp|Pro|Arg|Gly 445|Pro Gly Arg|
|Ala|Gln 450|Arg|Ser|Ala|Gly|Ala 455|Thr|Ala|Ala|Asp|Gly 460|Pro|Cys Ala Leu|
|Arg 465|Glu|Leu|Ser|Val|Asp 470|Leu|Arg|Ala|Glu|Arg 475|Ser|Val|Leu Ile Pro 480|
|Glu|Thr|Tyr|Gln|Ala 485|Asn|Asn|Cys|Gln|Gly 490|Val|Cys|Gly|Trp Pro Gln 495|
|Ser|Asp|Arg|Asn 500|Pro|Arg|Tyr|Gly|Asn 505|His|Val|Val|Leu 510|Leu Leu Lys|
|Met|Gln|Ala|Arg 515|Gly|Ala|Ala|Leu|Ala 520|Arg|Pro|Pro|Cys 525|Cys Val Pro|
|Thr|Ala|Tyr 530|Ala|Gly|Lys|Leu|Leu 535|Ile|Ser|Leu|Ser|Glu 540|Glu Arg Ile|
|Ser 545|Ala|His|His|Val|Pro 550|Asn|Met|Val|Ala|Thr 555|Glu|Cys|Gly Cys Arg 560|

( 2 ) INFORMATION FOR SEQ ID NO:2:

( i ) SEQUENCE CHARACTERISTICS:
        ( A ) LENGTH: 575 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Pro Gly Pro Ser Leu Ser Leu Ala Leu Val Leu Ser Ala Met Gly
1               5                   10                  15

Ala Leu Leu Arg Pro Gly Thr Pro Arg Glu Glu Val Phe Ser Thr Ser
            20                  25                  30

Ala Leu Pro Arg Glu Gln Ala Thr Gly Ser Gly Ala Leu Ile Phe Gln
            35                  40                  45

Gln Ala Trp Asp Trp Pro Leu Ser Ser Leu Trp Leu Pro Gly Ser Pro
    50                  55                  60

Leu Asp Pro Leu Cys Leu Val Thr Leu His Gly Ser Gly Asn Gly Ser
65                  70                  75                  80

Arg Ala Pro Leu Arg Val Val Gly Val Leu Ser Ser Tyr Glu Gln Ala
                85                  90                  95

Phe Leu Glu Ala Val Arg Arg Thr His Trp Gly Leu Ser Asp Leu Thr
            100                 105                 110

Thr Phe Ala Val Cys Pro Ala Gly Asn Gly Gln Pro Val Leu Pro His
            115                 120                 125

Leu Gln Arg Leu Gln Ala Trp Leu Gly Glu Pro Gly Gly Arg Trp Leu
    130                 135                 140

Val Val Leu His Leu Glu Val Thr Trp Glu Pro Thr Pro Leu Leu
145                 150                 155                 160

Arg Phe Gln Glu Pro Pro Pro Gly Gly Ala Ser Pro Pro Glu Leu Ala
                165                 170                 175

Leu Leu Val Val Tyr Pro Gly Pro Gly Leu Glu Val Thr Val Thr Gly
            180                 185                 190

Ala Gly Leu Pro Gly Thr Gln Ser Leu Cys Leu Thr Ala Asp Ser Asp
        195                 200                 205

Phe Leu Ala Leu Val Val Asp His Pro Glu Gly Ala Trp Arg Arg Pro
210                 215                 220

Gly Leu Ala Leu Thr Leu Arg Arg Arg Gly Asn Gly Ala Leu Leu Ser
225                 230                 235                 240

Thr Ala Gln Leu Gln Ala Leu Leu Phe Gly Ala Asp Ser Arg Cys Phe
            245                 250                 255

Thr Arg Lys Thr Pro Ala Leu Leu Leu Leu Leu Pro Ala Arg Ser Ser
            260                 265                 270

Ala Pro Met Pro Ala His Gly Arg Leu Asp Leu Val Pro Phe Pro Gln
        275                 280                 285

Pro Arg Ala Ser Pro Glu Pro Glu Glu Ala Pro Pro Ser Ala Asp Pro
    290                 295                 300

Phe Leu Glu Thr Leu Thr Arg Leu Val Arg Ala Leu Ala Gly Pro Pro
305                 310                 315                 320

Ala Arg Ala Ser Pro Pro Arg Leu Ala Leu Asp Pro Gly Ala Leu Ala
            325                 330                 335

Gly Phe Pro Gln Gly Gln Val Asn Leu Ser Asp Pro Ala Ala Leu Glu
            340                 345                 350

Arg Leu Leu Asp Gly Glu Glu Pro Leu Leu Leu Leu Pro Pro Thr
    355                 360                 365

Ala Ala Thr Thr Gly Val Pro Ala Thr Pro Gln Gly Pro Lys Ser Pro
    370                 375                 380

Leu Trp Ala Ala Gly Leu Ala Arg Arg Val Ala Ala Glu Leu Gln Ala
385                 390                 395                 400

Val Ala Ala Glu Leu Arg Ala Leu Pro Gly Leu Pro Pro Ala Ala Pro
            405                 410                 415

Pro Leu Leu Ala Arg Leu Leu Ala Leu Cys Pro Gly Asn Pro Asp Ser
            420                 425                 430
```

```
Pro  Gly  Gly  Pro  Leu  Arg  Ala  Leu  Leu  Leu  Lys  Ala  Leu  Gln  Gly
          435                 440                 445

Leu  Arg  Ala  Glu  Trp  Arg  Gly  Arg  Glu  Arg  Ser  Gly  Ser  Ala  Arg  Ala
     450                      455                      460

Gln  Arg  Ser  Ala  Gly  Ala  Ala  Ala  Asp  Gly  Pro  Cys  Ala  Leu  Arg
465                      470                 475                      480

Glu  Leu  Ser  Val  Asp  Leu  Arg  Ala  Glu  Arg  Ser  Val  Leu  Ile  Pro  Glu
                    485                 490                           495

Thr  Tyr  Gln  Ala  Asn  Asn  Cys  Gln  Gly  Ala  Cys  Gly  Trp  Pro  Gln  Ser
               500                 505                      510

Asp  Arg  Asn  Pro  Arg  Tyr  Gly  Asn  His  Val  Val  Leu  Leu  Leu  Lys  Met
          515                 520                      525

Gln  Ala  Arg  Gly  Ala  Thr  Leu  Ala  Arg  Pro  Pro  Cys  Cys  Val  Pro  Thr
530                      535                      540

Ala  Tyr  Thr  Gly  Lys  Leu  Leu  Ile  Ser  Leu  Ser  Glu  Glu  Arg  Ile  Ser
545                      550                      555                      560

Ala  His  His  Val  Pro  Asn  Met  Val  Ala  Thr  Glu  Cys  Gly  Cys  Arg
                    565                      570                      575
```

( 2 ) INFORMATION FOR SEQ ID NO:3:

( i ) SEQUENCE CHARACTERISTICS:
        ( A ) LENGTH: 553 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met  Gln  Gly  Pro  His  Leu  Ser  Leu  Leu  Leu  Leu  Leu  Ala  Thr  Met
1                   5                   10                      15

Gly  Ala  Val  Leu  Gln  Ala  Asp  Thr  Val  Glu  Glu  Leu  Thr  Asn  Thr  Arg
               20                 25                      30

Gly  Leu  Ile  Phe  Leu  Glu  Asp  Gly  Val  Trp  Pro  Ser  Ser  Pro  Pro
          35                 40                      45

Glu  Pro  Leu  Cys  Leu  Val  Ala  Val  Arg  Gly  Glu  Gly  Asp  Thr  Ser  Lys
     50                 55                      60

Ala  Ser  Leu  Thr  Val  Val  Gly  Gly  Leu  His  Ser  Tyr  Glu  Gln  Ala  Phe
65                      70                 75                           80

Leu  Glu  Ala  Val  Gln  Glu  Ser  Arg  Trp  Gly  Pro  Gln  Asp  Leu  Ala  Thr
                    85                      90                      95

Phe  Gly  Val  Cys  Ser  Thr  Asp  Ser  Gln  Thr  Thr  Leu  Pro  Ala  Leu  Gln
               100                 105                      110

Arg  Leu  Gly  Ala  Trp  Leu  Gly  Glu  Thr  Gly  Glu  Gln  Gln  Leu  Leu  Val
          115                 120                      125

Leu  His  Leu  Ala  Glu  Val  Ile  Trp  Glu  Pro  Gln  Leu  Leu  Leu  Lys  Phe
     130                 135                      140

Gln  Glu  Pro  Pro  Pro  Gly  Gly  Ala  Ser  Arg  Trp  Glu  Gln  Ala  Leu  Leu
145                      150                      155                      160

Val  Leu  Tyr  Pro  Gly  Pro  Gly  Pro  Gln  Val  Thr  Val  Thr  Gly  Ala  Gly
               165                 170                      175

Leu  Gln  Gly  Thr  Gln  Ser  Leu  Cys  Pro  Thr  Arg  Asp  Thr  Arg  Tyr  Leu
          180                 185                      190

Val  Leu  Thr  Val  His  Phe  Pro  Ala  Gly  Ala  Trp  Ser  Gly  Ser  Gly  Leu
     195                 200                      205

Ala  Leu  Thr  Leu  Gln  Pro  Ser  Lys  Glu  Gly  Ala  Thr  Leu  Thr  Ile  Ala
210                      215                      220
```

-continued

```
Gln  Leu  Gln  Ala  Phe  Leu  Phe  Gly  Ser  Asp  Ser  Arg  Cys  Phe  Thr  Arg
225                      230                      235                      240

Lys  Thr  Pro  Thr  Leu  Val  Leu  Pro  Pro  Thr  Gly  Pro  Thr  Pro  Gln
                    245                      250                      255

Pro  Ala  His  Gly  Gln  Leu  Asp  Thr  Val  Pro  Phe  Pro  Gln  Pro  Gly  Leu
               260                      265                      270

Ser  Leu  Glu  Pro  Glu  Asp  Leu  Pro  His  Ser  Ala  Asp  Pro  Phe  Leu  Glu
          275                      280                      285

Thr  Leu  Thr  Arg  Leu  Val  Arg  Ala  Leu  Arg  Gly  Pro  Leu  Thr  Arg  Ala
          290                      295                      300

Ser  Asn  Thr  Arg  Leu  Ala  Leu  Asp  Pro  Gly  Ala  Leu  Ala  Ser  Phe  Pro
305                      310                      315                      320

Gln  Gly  Leu  Val  Asn  Leu  Ser  Asp  Pro  Val  Ala  Leu  Gly  Arg  Leu  Leu
                    325                      330                      335

Asp  Gly  Glu  Glu  Pro  Leu  Leu  Leu  Leu  Leu  Ser  Pro  Ala  Ala  Ala  Thr
               340                      345                      350

Val  Gly  Glu  Pro  Met  Arg  Leu  His  Ser  Pro  Thr  Ser  Ala  Pro  Trp  Ala
          355                      360                      365

Ala  Gly  Leu  Ala  Arg  Arg  Val  Ala  Val  Glu  Leu  Gln  Ala  Ala  Ala  Ser
     370                      375                      380

Glu  Leu  Arg  Asp  Leu  Pro  Gly  Leu  Pro  Pro  Thr  Ala  Pro  Pro  Leu  Leu
385                      390                      395                      400

Ser  Arg  Leu  Leu  Ala  Leu  Cys  Pro  Asn  Asp  Ser  Arg  Ser  Ala  Gly  Asp
                    405                      410                      415

Pro  Leu  Arg  Ala  Leu  Leu  Leu  Lys  Ala  Leu  Gln  Gly  Leu  Arg  Ala
               420                      425                      430

Glu  Trp  Arg  Gly  Arg  Glu  Gly  Arg  Gly  Arg  Ala  Gly  Arg  Ser  Lys  Gly
          435                      440                      445

Thr  Gly  Thr  Asp  Gly  Leu  Cys  Ala  Leu  Arg  Glu  Leu  Ser  Val  Asp  Leu
     450                      455                      460

Arg  Ala  Glu  Arg  Ser  Val  Leu  Ile  Pro  Glu  Thr  Tyr  Gln  Ala  Asn  Asn
465                      470                      475                      480

Cys  Gln  Gly  Ala  Cys  Gly  Trp  Pro  Trp  Ser  Asp  Arg  Asn  Pro  Arg  Tyr
               485                      490                      495

Gly  Asn  His  Val  Val  Leu  Leu  Leu  Lys  Met  Gln  Ala  Arg  Gly  Ala  Ala
               500                      505                      510

Leu  Gly  Arg  Leu  Pro  Cys  Cys  Val  Pro  Thr  Ala  Tyr  Thr  Gly  Lys  Leu
          515                      520                      525

Leu  Ile  Ser  Leu  Ser  Glu  Glu  His  Ile  Ser  Ala  His  His  Val  Pro  Asn
     530                      535                      540

Met  Val  Ala  Thr  Glu  Cys  Gly  Cys  Arg
545                      550
```

( 2 ) INFORMATION FOR SEQ ID NO:4:

( i ) SEQUENCE CHARACTERISTICS:
  ( A ) LENGTH: 10 amino acids
  ( B ) TYPE: amino acid
  ( D ) TOPOLOGY: linear ( i i ) MOLECULE TYPE: protein ( x i ) SEQUENCE DESCRIPTION: SEQ ID NO:4:

```
Leu  Arg  Ala  Glu  Glu  Pro  Ala  Val  Gly  Thr
1                  5                        10
```

( 2 ) INFORMATION FOR SEQ ID NO:5:

( i ) SEQUENCE CHARACTERISTICS:

(A) LENGTH: 10 amino acids
(B) TYPE: amino acid
(D) TOPOLOGY: linear (ii) MOLECULE TYPE: protein (xi) SEQUENCE DESCRIPTION: SEQ ID NO:5:

Ala Ala Gly Ala Thr Ala Ala Asp Gly Pro
1               5                   10

(2) INFORMATION FOR SEQ ID NO:6:

(i) SEQUENCE CHARACTERISTICS:
(A) LENGTH: 5 amino acids
(B) TYPE: amino acid
(D) TOPOLOGY: linear (ii) MOLECULE TYPE: protein (xi) SEQUENCE DESCRIPTION: SEQ ID NO:6:

Arg Gly Glu Asp Ser
1               5

(2) INFORMATION FOR SEQ ID NO:7:

(i) SEQUENCE CHARACTERISTICS:
(A) LENGTH: 4 amino acids
(B) TYPE: amino acid
(D) TOPOLOGY: linear (ii) MOLECULE TYPE: protein (xi) SEQUENCE DESCRIPTION: SEQ ID NO:7:

Arg Gly Asp Ser
1